(12) United States Patent
Harada et al.

(10) Patent No.: US 10,583,075 B2
(45) Date of Patent: Mar. 10, 2020

(54) COMPOSITION COMPRISING A HYDROPHOBICALLY MODIFIED INULINE AND A POLYETHER MODIFIED SILICONE

(71) Applicant: L'OREAL, Paris (FR)

(72) Inventors: Yasuko Harada, Kawasaki (JP); Toru Koike, Kawasaki (JP); Kyoko Amazaki, Kawasaki (JP); Didier Candau, Bievres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/753,501

(22) PCT Filed: Aug. 16, 2016

(86) PCT No.: PCT/JP2016/003747
§ 371 (c)(1),
(2) Date: Feb. 19, 2018

(87) PCT Pub. No.: WO2017/029807
PCT Pub. Date: Feb. 23, 2017

(65) Prior Publication Data
US 2018/0243197 A1    Aug. 30, 2018

(30) Foreign Application Priority Data

Aug. 20, 2015    (JP) ................................. 2015-162534

(51) Int. Cl.
| | | |
|---|---|---|
| *A61K 8/29* | (2006.01) | |
| *A61K 8/49* | (2006.01) | |
| *A61K 8/58* | (2006.01) | |
| *A61K 8/73* | (2006.01) | |
| *A61Q 17/04* | (2006.01) | |
| *A61K 8/37* | (2006.01) | |
| *A61K 8/894* | (2006.01) | |
| *A61P 17/16* | (2006.01) | |
| *A61K 8/06* | (2006.01) | |

(52) U.S. Cl.
CPC ............... *A61K 8/73* (2013.01); *A61K 8/062* (2013.01); *A61K 8/29* (2013.01); *A61K 8/37* (2013.01); *A61K 8/4966* (2013.01); *A61K 8/585* (2013.01); *A61K 8/894* (2013.01); *A61P 17/16* (2018.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 2006/0204468 A1* | 9/2006 | Allef | .................... | A61K 8/0208 |
| | | | | 424/70.13 |
| 2014/0294743 A1* | 10/2014 | Richard | ................... | A61K 8/41 |
| | | | | 424/59 |
| 2014/0323431 A1* | 10/2014 | Lorant | ................. | A61K 8/8158 |
| | | | | 514/54 |

FOREIGN PATENT DOCUMENTS

| | | |
|---|---|---|
| JP | 2009-191033 A | 8/2009 |
| KR | 2005 0013680 A | 2/2005 |
| KR | 2015 0078973 A | 7/2015 |
| WO | WO 2009/080659 A2 | 7/2009 |

OTHER PUBLICATIONS

International Search Report (PCT/ISA/210) dated Nov. 21, 2016, by the Japanese Patent Office as the International Searching Authority for International Application No. PCT/JP2016/003747.
Written Opinion (PCT/ISA/237) dated Nov. 21, 2016, by the Japanese Patent Office as the International Searching Authority for International Application No. PCT/JP2016/003747.
Tadros, T.F. et al., "Chapter 4, Enhancement of Stabilization and Performance of Personal Care Formulations using Polymeric Surfactants, Emulsion Science and Technology", pp. 75-81, Dec. 31, 2009, XP009192345.
Booten, K. et al., "Nature-based emulsifiers & their cosmetic applications", HAPPI Household and Personal Products Industry, vol. 41, No. 3, pp. 66-67, Mar. 1, 2004, XP009132712.
Levecke, B. et al., "Nano-emulsions based on inulin surfactants for personal care formulations", SOFW-Journal Seifen, vol. 132, No. 6, pp. 24-26, 28, Jun. 1, 2006, XP001538873.

\* cited by examiner

*Primary Examiner* — Brian Gulledge
(74) *Attorney, Agent, or Firm* — Buchanan, Ingersoll & Rooney PC

(57) ABSTRACT

The present invention relates to a composition in the form of an oil-in-water emulsion comprising a) at least one hydrophobically modified inulin, b) at least one polyether modified silicone and c) at least one UV filter, in which the hydrophobically modified inulin is present in a content ranging from about 0.01 to about 10% by weight relative to the total weight of the composition. The composition of the present invention has good skin affinity and homogeneous spreading, and maintains further good watery skin sensation.

19 Claims, No Drawings

COMPOSITION COMPRISING A HYDROPHOBICALLY MODIFIED INULINE AND A POLYETHER MODIFIED SILICONE

TECHNICAL FIELD

The present invention relates to a composition in the form of an oil-in-water emulsion containing a hydrophobically modified inulin, a polyether modified silicone and a UV filter.

BACKGROUND ART

Currently, an oil-in-water (O/W) emulsion and a water-in-oil (W/O) emulsion are used widely for the reasons that they can provide the skin with greater comfort of use (e.g., softness and emollience). The O/W emulsion consists of an aqueous continuous phase and an oily dispersed phase, and the W/O emulsion consists of an oily continuous phase and an aqueous dispersed phase. The O/W emulsion is more preferred in the cosmetics field, since it comprises an aqueous phase as the external phase, which gives the skin a fresher, less greasy and lighter feel than the W/O emulsion.

For example, WO2009/080659 discloses an O/W emulsion containing a hydrophobically modified inulin and at least one thickening polysaccharide of plant origin, which has good stability even without conventional surfactants such as polyglyceryl ester. Further such an O/W emulsion brings good watery skin sensation and non-sticky after feel.

SUMMARY OF INVENTION

Problems to be Solved by the Invention

However, such an O/W emulsion containing a hydrophobically modified inulin is not entirely satisfactory, since it has weak skin affinity and inhomogeneous spreading. In consequence, in case such an O/W emulsions contains a lipophilic cosmetic or dermatological ingredient such as a UV filter, the application of the O/W emulsions to the skin becomes uneven and the efficacy thereof is significantly decreased. To solve the problems, currently several types of surfactants such as glyceryl stearate, potassium cetyl phosphate and behenyl alcohol are used for O/W emulsions. These surfactants improve the skin affinity and the inhomogeneous spreading, but adversely affect watery skin sensation of the O/W emulsions.

Means to Solve the Problems

The inventors have found that, a combination of a hydrophobically modified inulin and a polyether modified silicone improves the skin affinity and inhomogeneous spreading without adversely affecting watery skin sensation of the O/W emulsions.

Thus, in one aspect of the present invention, there is provided a composition in the form of an oil-in-water emulsion containing a) at least one hydrophobically modified inulin,
b) at least one polyether modified silicone, and
c) at least one UV filter.

In the above aspects, it is preferable that the hydrophobically modified inulin is present in a content ranging from about 0.01 to about 10% by weight, preferably from about 0.1 to about 5% by weight, in particular from about 0.15 to about 3% by weight relative to the total weight of the composition.

In the above aspects, it is preferable that a hydrophobic group in the hydrophobically modified inulin is selected from alkyl carbamate groups, preferably $C_4$-$C_{32}$ alkyl carbamate groups or alkyl ester groups, preferably $C_4$-$C_{32}$ alkyl ester groups, more preferably from $C_{10}$-$C_{18}$ alkyl carbamate groups or $C_{10}$-$C_{18}$ alkyl ester groups.

In the above aspects, it is preferable that the hydrophobically modified inulin is based on chicory inulin, preferably is inulin lauryl carbamate.

In the above aspects, it is also preferable that the polyether modified silicone is present in a content ranging from about 0.01 to about 10% by weight, preferably from about 0.05 to about 5% by weight, in particular from about 0.1 to about 2% by weight relative to the total weight of the composition.

In the above aspects, it is also preferable that the polyether modified silicone is a silicone having a monovalent group selected from polyoxyalkylene groups, preferably polyoxy $C_2$-$C_8$ alkylene groups, in particular a polyoxyethylene group, a polyoxypropylene group or a polyoxybutylene group.

In the above aspects, it is also preferable that the polyether modified silicone is selected from polyoxyethylene modified dimethicones.

In the above aspects, it is also preferable that the UV filter is present in a content ranging from about 0.01 to about 30% by weight, preferably from about 0.1 to about 25% by weight, in particular from about 5 to about 20% by weight relative to the total weight of the composition.

In the above aspects, it is also preferable that the UV filter is an organic UV filter, or is a combination of an organic UV filter and an inorganic UV filter.

In the above aspects, it is also preferable that the UV filter is selected from the group consisting of drometrizole trisiloxane, ethylhexyl methoxycinnamate, bis-ethylhexyloxyphenol methoxyphenyl triazine, $TiO_2$ and mixtures thereof.

In the above aspects, it is also preferable that the composition contains water in a content ranging from 50 to 95% by weight, preferably from 60 to 90% by weight, and more preferably from 65 to 90% by weight, relative to the total weight of the composition.

In another aspect of the present invention, there is provided a method of protecting a keratin substance from ultraviolet radiation comprising applying to the keratin substance the composition according to the above.

In another aspect of the present invention, there is provided a method of absorbing ultraviolet light comprising applying the composition according to the above to a keratin substance and subjecting the keratin substance to ultraviolet light.

In another aspect of the present invention, there is provided use of the composition according to the above for protecting a keratin substance from ultraviolet radiation.

In another aspect of the present invention, there is provided use of the composition according to the above for absorbing ultraviolet light.

Effects of the Invention

The composition in the form of an O/W emulsion of the present invention has good skin affinity and good homogeneous spreading, and maintains further good watery skin sensation. Therefore, even if the composition further contains lipophilic cosmetic or dermatological ingredients such as a UV filter, the application of the composition to the skin becomes uniform and the intact efficacy thereof can be expected.

Embodiments to Carry Out the Invention

<Composition in the Form of an Oil in Water Emulsion>

The composition of the present invention contains a) at least one hydrophobically modified inulin, b) at least one polyether modified silicone and c) at least one UV filter.

a) Hydrophobically Modified Inulin

The composition of the present invention contains at least one hydrophobically modified inulin. According to the present invention, the term "hydrophobically modified inulin" especially means an inulin modified with hydrophobic chains, in particular modified by grafting hydrophobic chains onto the hydrophilic backbone of the said inulin.

Inulin is part of the fructan family. Fructans or fructosans are oligosaccharides or polysaccharides comprising a sequence of anhydro fructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatically.

Fructans generally have a degree of polymerization from 2 to about 1000 and preferably from 2 to about 60.

Three groups of fructans are distinguished. The first group corresponds to products whose fructose units are for the most part linked via β-2-1 bonds. These are essentially linear fructans such as inulin. The second group also corresponds to linear fructoses, but the fructose units are essentially linked via β-2-6 bonds. These products are levans. The third group corresponds to mixed fructans, i.e. containing β-2-6 and β-2-1 sequences. These are essentially branched fructans, such as graminans.

Inulin may be obtained, for example, from chicory, dahlia or Jerusalem artichoke. In the context of the present invention, the hydrophobically modified inulin is preferentially obtained from chicory.

The inulins used in the compositions of the present invention are hydrophobically-modified. In particular, they are obtained by grafting hydrophobic chains onto the hydrophilic backbone of the fructan.

The hydrophobic chains that may be grafted onto the main chain of the fructan may especially be linear or branched, saturated or unsaturated hydrocarbon-based chains containing from 1 to 50 carbon atoms, such as alkyl, arylalkyl, alkylaryl or alkylene groups; divalent cycloaliphatic groups or organopolysiloxane chains. These hydrocarbon-based or organopolysiloxane chains may especially comprise one or more ester, amide, urethane, carbamate, thiocarbamate, urea, thiourea and/or sulfonamide functions especially such as methylenedicyclohexyl and isophorone; or divalent aromatic groups such as phenylene.

According to a particular embodiment, the hydrophobically modified inulin(s) used in the context of the present invention are inulins bearing hydrophobic groups chosen from hydrophobic carbamate or ester groups.

The term "hydrophobic carbamate group" means a $C_4$-$C_{32}$ alkyl carbamate group, i.e. a group —OCONH—R, R being a $C_4$-$C_{32}$ alkyl group. The term "hydrophobic ester group" means a $C_4$-$C_{32}$ alkyl ester group, i.e. a group —OCO—R, R being a $C_4$-$C_{32}$ alkyl group.

These hydrophobic groups are especially derived from the reaction of the hydroxyl groups of the starting inulin with either an isocyanate R—N=C=O (to form a carbamate group) or an acid R—COOH or acid chloride R—COCl (to form an ester group).

In particular, the inulin has a degree of polymerization from 2 to about 1000, preferably from 2 to about 100 and even more preferentially from 2 to about 70, and a degree of substitution of less than 2 on the basis of a fructose unit.

Advantageously, the hydrophobic carbamate group is a $C_6$-$C_{20}$ alkyl carbamate group. Preferably, the hydrophobic carbamate group is a $C_8$-$C_{18}$ alkyl carbamate group. Preferentially, the hydrophobic carbamate group is a $C_{10}$-$C_{18}$ alkyl carbamate group. More preferentially, the hydrophobic carbamate group is a $C_{10}$-$C_{14}$ alkyl carbamate group.

According to a more preferred embodiment, the hydrophobic carbamate group is a lauryl carbamate group ($C_{12}$ alkyl group).

Inulins bearing hydrophobic carbamate groups are described, for example, in published patent applications WO 99/64549 and WO 2009/080661.

Advantageously, the hydrophobic ester group is a $C_6$-$C_{20}$ alkyl ester group. Preferably, the hydrophobic ester group is a $C_8$-$C_{20}$ alkyl ester group. Preferentially, the hydrophobic ester group is a $C_{10}$-$C_{20}$ alkyl ester group. More preferentially, the hydrophobic ester group is a $C_{10}$-$C_{18}$ alkyl ester group.

Inulins bearing hydrophobic ester groups are described, for example, in U.S. Pat. No. 5,877,144.

In particular, the hydrophobic groups of inulin are chosen from $C_4$-$C_{32}$ alkyl carbamate or $C_4$-$C_{32}$ alkyl ester groups, preferably from $C_{10}$-$C_{18}$ alkyl carbamate or $C_{10}$-$C_{18}$ alkyl ester groups.

Preferably, an inulin bearing hydrophobic carbamate groups is used.

The inulin bearing hydrophobic carbamate or ester groups may have a degree of substitution (proportion of OH of the inulin substituted with a hydrophobic group) ranging from 0.01 to 0.5, preferably ranging from 0.02 to 0.4 and preferentially ranging from 0.05 to 0.35. Advantageously, the degree of substitution may range from 0.1 to 0.3.

Examples of an inulin bearing a hydrophobic ester group include stearoyl inulin, such as the products sold under the names Lifidrem INST(registered trademark) by the company Engelhard and Rheopearl INS(registered trademark) by the company Ciba; palmitoyl inulin; undecylenoyl inulin, such as the products sold under the names Lifidrem INUK(registered trademark) and Lifidrem INUM(registered trademark) by the company Engelhard.

A preferred example of an inulin bearing hydrophobic carbamate group is inulin lauryl carbamate, such as the product sold under the name Inutec SP1(registered trademark) by the company Beneo and Inutec SL1(registered trademark) by the company Creachem.

Preferably, the hydrophobically modified inulin in the composition of the present invention is based on chicory inulin and in particular is inulin lauryl carbamate.

According to a particular embodiment, the amount of hydrophobically modified inulin in the composition of the present invention may range from about 0.01 to about 10% by weight, preferably from about 0.1 to about 5% by weight, in particular from about 0.15 to about 3% by weight relative to the total weight of the composition.

Preferably, the ratio of the amount of oily phase to the amount of hydrophobically modified inulin may range from 50 to 200 and preferably from 50 to 150.

b) Polyether Modified Silicone

The composition of the present invention also contains at least one polyether modified silicone. According to the present invention, the term "polyether modified silicone" especially means a copolymer having a hydrophobic polyorganosiloxane chain and a hydrophilic polyoxyalkylene group. A polyoxyalkylene group is preferably introduced onto a terminal and/or a side chain of a polyorganosiloxane chain.

Examples of a polyoxyalkylene group include polyoxy $C_2$-$C_8$ alkylene groups, preferably a polyoxyethylene (i.e., PEG) group, a polyoxypropylene (i.e., PPG) group or a polyoxybutylene group, in particular a polyoxyethylene (PEG) group. The polyoxyalkylene group preferably contains a number of moles of oxyalkylene groups or units of between 1 and 50, more preferably between 2 and 30, and most preferably between 2 and 15.

Examples of polyether modified silicones include a polyoxyethylene-methylpolysiloxane copolymer, a polyoxypropylene-methylpolysiloxane copolymer, preferably polyoxyethylene modified dimethicones, in particular PEG-3 dimethicone, PEG-9 dimethicone, PEG-10 dimethicone, PEG-11 dimethicone, PEG-12 dimethicone, PEG-9 methyl ether dimethicone, PEG-11 methyl ether dimethicone, PEG-32 methyl ether dimethicone, PEG-9 polydimethylsiloxyethyl dimethicone, lauryl PEG-9 polydimethylsiloxyethyl dimethicone and PEG/PPG-20/22 butyl ether dimethicone, each of which is an INCI name.

The polyether modified silicones used in the compositions of the present invention can be commercially available products. Examples of such products include SH3771M, SH3772M, SH3773M, SH3775M, SH3749, BY22-008, BY25-337, BY25-339, FZ-2222, FZ-2233, FZ-2250 by the company Dow Corning Toray; KF-6011, KF-6012, KF-6013, KF-6015, KF-6016, KF-6017, KF-6004, KF-6028, KF-6038, KF-6043 by the company Shin-Etsu Chemical; TSF4440, SF1188A, SILSOFT305, SILSOFT430, SILSOFT440, SILSOFT475, SILSOFT805, SILSOFT810, SILSOFT840, SILSOFT870, SILSOFT875, SIOSOFT880, SILSOFT895 by the company Momentive Performance Materials Japan, each of which is a trade name.

The polyether modified silicones can be used alone or in combination with two or more polyether modified silicones. It is preferable to use two or more polyether modified silicones in combination. By combining two or more polyether modified silicones, the efficacy of antisun compositions expressed by the sun protection factor (SPF) can be synergistically improved.

According to a particular embodiment, the amount of polyether modified silicone in the composition of the present invention may range from about 0.01 to about 10% by weight, preferably from about 0.05 to about 5% by weight, in particular from about 0.1 to about 2% by weight relative to the total weight of the composition.

c) UV Filter

The composition of the present invention contains at least one UV filter. If two or more UV filters are used, they may be the same or different.

The UV filter can be selected from inorganic UV filters, organic UV filters, and mixtures thereof. The UV filter used in the composition of the present invention may be active in the UV-A and/or UV-B region. The UV filter may be hydrophilic and/or lipophilic.

According to a particular embodiment, the total amount of the UV filter in the composition of the present invention may range from about 0.01 to about 30% by weight, preferably from about 0.1 to about 25% by weight, in particular from about 5 to about 20% by weight relative to the total weight of the composition.

The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filters, of those denoted below under their INCI names, and mixtures thereof.

Anthranilic compounds: Methyl anthranilate, marketed under the trademark "Neo Heliopan MA" by Haarmann and Reimer.

Dibenzoylmethane compounds: Butyl methoxydibenzoylmethane, marketed in particular under the trademark "Parsol 1789" by Hoffmann-La Roche; and isopropyl dibenzoylmethane.

Cinnamic compounds: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomenthyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophenone sulfonic acid), marketed under the trademark "Uvinul MS40"

by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethylamino-2-hydroxybenzoyl)benzoate (UVINUL A+ by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark "TINOSORB(registered trademark) S" by BASF, and ethylhexyl triazine marketed under the trademark "UVINUL(registered trademark) T150" by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-La Roche.

Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol]marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or "Mexoryl XL" by L'Oreal, as represented below.

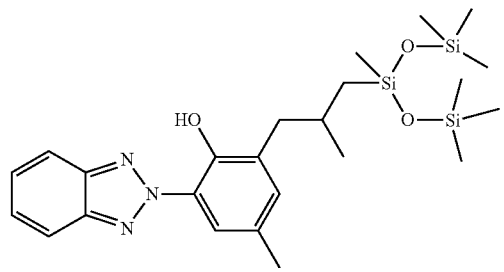 [SMILES: Cc1cc(CC(C)C[Si](C)(O[Si](C)(C)C)O[Si](C)(C)C)c(O)c(-n2nc3ccccc3n2)c1]

Benzoxazole compounds: 2,4-bis[5-1 (dimethylpropyl) benzoxazol-2-yl-(4-phenyl)imino]-6-(2-ethylhexyl) imino-1,3,5-triazine, marketed under the trademark Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds: 1,1-dicarboxy(2,2'-dimethylpropyl)-4,4-diphenylbutadiene.

According to a particular embodiment, the amount of an organic UV filter in the composition of the present invention may range from 1 to about 30% by weight, preferably from about 1 to about 25% by weight, in particular from about 1 to about 20% by weight relative to the total weight of the composition.

It is preferable that the inorganic UV filter be in the form of a fine particle such that the mean (primary) particle diameter thereof ranges from 1 nm to 50 µm, preferably 5 nm to 500 nm, and more preferably 10 nm to 200 nm. The mean (primary) particle size or mean (primary) particle diameter here is an arithmetic mean diameter.

The inorganic UV filter can be selected from the group consisting of silicon carbide, metal oxides which may or may not be coated, and mixtures thereof.

Examples of the inorganic UV filter include inorganic pigments based on metal oxides and/or other metal compounds which are insoluble or sparingly soluble in water and are coated or uncoated. Examples of metal oxides include titanium oxide (e.g. $TiO_2$), zinc oxide (e.g. ZnO), iron oxide (e.g. $Fe_2O_3$), zirconium oxide (e.g. $ZrO_2$), silicon oxide ($SiO_2$), manganese oxide (e.g. MnO), aluminum oxide (e.g. $Al_2O_3$), cerium oxide (e.g. $Ce_2O_3$), mixed oxides of the corresponding metals and mixtures of such oxides. The inorganic UV filter is more preferably at least one metal oxide selected from the group consisting of titanium dioxide ($TiO_2$), zinc oxide (ZnO) and aluminum oxide ($Al_2O_3$).

In one embodiment, the inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds. Preferably, Stearic acid (and) Aluminum Hydroxide (and) $TiO_2$, such as the product "MT-100 TV" from Tayca can be used as the inorganic UV filter.

According to a particular embodiment, the amount of the inorganic UV filter in the composition of the present invention may range from 0 to about 10% by weight, preferably from about 0.1 to about 5% by weight, in particular from about 1 to about 3% by weight relative to the total weight of the composition.

O/W Emulsion

The composition of the present invention is in the form of an oil-in-water (O/W) emulsion, which basically consists of an aqueous continuous phase and an oily dispersed phase. The three essential components of the present invention: a) hydrophobically modified inulin, b) polyether modified silicone and c) UV filter can be contained in either one or both of the phases, depending on the nature of each component.

Aqueous Phase

In addition, the aqueous phase of the composition according to the present invention contains water and optionally one or more water-miscible or at least partially water-miscible compounds, for instance $C_2$ to $C_8$ lower polyols or monoalcohols, such as ethanol and isopropanol.

The term "polyol" should be understood as meaning any organic molecule comprising at least two free hydroxyl groups. Examples of polyols include glycols, for instance butylene glycol, propylene glycol, and isoprene glycol, glycerol and polyethylene glycols, for instance PEG-8, sorbitol and sugars, for instance glucose.

The aqueous phase may also comprise any common water-soluble or water-dispersible additives as mentioned below.

The aqueous phase may be present in a content ranging from about 30 to about 98% by weight, preferably from about 30 to about 95% by weight, better still from about 30 to about 90% by weight and even better still from about 35 to about 85% by weight relative to the total weight of the composition.

The water-miscible compound(s), such as lower polyols and alcohols, may be present in an amount ranging from 0 to about 30%, especially from about 0.1% to about 30% and better still in an amount ranging from about 1% to about 20%, relative to the total weight of the composition.

The composition of the present invention comprises water preferably in a content ranging from 50 to 95% by weight, preferably from 60 to 90% by weight, and more preferably from 65 to 90% by weight, relative to the total weight of the composition.

This amount of aqueous phase does not contain the amount of three essential components of: a) hydrophobically modified inulin, b) polyether modified silicone and c) UV filter.

Oily Phase

The nature of the oily phase of the composition according to the present invention is not critical. The oily phase is a fatty phase containing at least one fatty substance chosen from fatty substances that are liquid at room temperature and volatile or non-volatile oils of plant, mineral or synthetic origin, and mixtures thereof. These oils are physiologically acceptable.

The term "room temperature" should be understood as meaning a temperature of about 25° C., at normal atmospheric pressure (760 mmHg).

The oily phase may also contain any common liposoluble or lipodispersible additive as mentioned below as mentioned below. It may especially comprise other fatty substances such as waxes, pasty compounds, fatty alcohols or fatty acids. The oily phase contains at least one oil, more particularly at least one cosmetic oil.

The term "oil" means a fatty substance that is liquid at room temperature.

According to a preferred embodiment, the composition of the present invention comprises at least one oil chosen from silicone oils, linear or branched hydrocarbons, synthetic ethers and esters, and mixtures thereof and is especially chosen from volatile silicone oils and branched hydrocarbons, for instance Parleam$^{(registered\ trademark)}$ oil, and mixtures thereof.

The amount of oily phase in the composition of the invention is less than about 35% of the total weight of the composition.

The amount of oily phase may range, for example, from 0 to about 30% by weight and preferably from about 1 to 20% by weight relative to the total weight of the composition.

This amount of oily phase does not contain the amount of three essential components of: a) hydrophobically modified inulin, b) polyether modified silicone and c) UV filter.

Additives

In a known manner, the composition of the present invention may also contain one or more adjuvants, UV boosters and/or active ingredients that are common in cosmetics or dermatology.

Adjuvants

Examples of adjuvants include gelling agents (e.g., xanthan gum, etc.), preserving agents (e.g., phenoxyethanol, etc.), sequestering agents (e.g., ethylene diamine tetraacetic acid, i.e., EDTA, or its salt etc.), emulsion stabilizers (e.g., ammonium polyacryloyldimethyltautrate, etc.), antioxidants, fragrances, solvents, salts, fillers, dyestuffs, basic agents (e.g., triethanolamine, diethanolamine or sodium hydroxide, etc.) or acidic agents (e.g., citric acid, etc.), and also lipid vesicles or any other type of vector c and mixtures thereof.

These adjuvants are used in the usual proportions in the cosmetics field, for example from about 0.01 to about 30% of the total weight of the composition, and, depending on their nature, they are introduced into the aqueous phase or into the oily phase of the composition, or alternatively into vesicles or any other type of vector.

UV Boosters

The composition of the present invention may further comprise one or more UV boosters. "UV booster" means each organic or inorganic, non polymeric or polymeric compound cable of increasing the Sun Protection Factor and/or the PPD Index (UVA protection index) of a composition containing at least one UV filter.

The efficacy of antisun compositions is generally expressed by the sun protection factor (SPF), which is expressed mathematically by the ratio of the dose of UV radiation necessary to reach the erythemogenic threshold with the UV screening agent to the dose of UV radiation necessary to reach the erythemogenic threshold without UV screening agent. This factor thus relates to the effectiveness of the protection with respect to erythema, the spectrum of biological action of which is centered in the UV-B region, and consequently describes the protection with respect to this UV-B radiation.

In view of the effects of UV-A radiation on the skin and of the development of numerous compositions comprising combinations of screening agents capable of absorbing UV-B and/or UV-A radiation, specific methods for evaluating protection against UV-A radiation have been developed. For the characterization of protection with respect to UV-A radiation, the PPD (Persistent Pigment Darkening) method, which measures the colour of the skin observed 2 to 4 hours after exposure of the skin to UV-A radiation, is particularly recommended and used. This method was adopted in 1996 by the Japanese Cosmetic Industry Association (JCIA) as official test procedure for the UV-A labelling of products and is frequently used by test laboratories in Europe and the United States (Japan Cosmetic Industry Association Technical Bulletin. Measurement Standards for UVA protection efficacy. Issued Nov. 21, 1995 and effective of Jan. 1, 1996).

The sun protection factor UV-APPD (UV-APPD PF) is expressed mathematically by the ratio of the dose of UV-A radiation necessary to reach the pigmentation threshold with the UV screening agent (MPPDp) to the dose of UV-A radiation necessary to reach the pigmentation threshold without UV screening agent (MPPDnp).

UV-AppD PF=MPPDp/MPPDnp

Mentions may be made of the UV booster such as styrene/acrylates copolymer that are marketed, for example under the tradename SunspheresT Powder by the company Rohm and Haas (Dow Chemical), oil thickeners (e.g., dextrin palmitate), surfactants and film formers (e.g., ammonium acryloyldimethyltaurate/vp copolymer).

Active Ingredients

Examples of active ingredients include moisturizers such as protein hydrolysates; sodium hyaluronate; polyols (e.g., glycerol, glycols such as polyethylene glycols, and sugar derivatives); anti-inflammatory agents; procyannidol oligomers; vitamins (e.g., vitamin A (retinol), vitamin E (tocopherol), vitamin K, vitamin C (ascorbic acid), vitamin B5 (panthenol), vitamin B3 or PP (niacinamide)), derivatives of these vitamins (especially esters) and mixtures thereof; keratolytic agents and/or desquamating agents, such as salicylic acid and its derivatives, α-hydroxy acids (e.g., lactic acid and glycolic acid) and derivatives thereof, and ascorbic acid and its derivatives; urea; caffeine; depigmenting agents (e.g., kojic acid, hydroquinone and caffeic acid); salicylic acid and its derivatives; retinoids (e.g., carotenoids) and vitamin A derivatives; hydrocortisone; melatonin; algal extracts, fungal extracts, plant extracts, yeast extracts or bacterial extracts; steroids; antibacterial active agents (e.g., 2,4,4'-trichloro-2'-hydroxydiphenyl ether (or triclosan), 3,4, 4'-trichlorocarbanilide (or triclocarban)); the acids indicated above, and especially salicylic acid and its derivatives; nucleotides (e.g., adenosine); enzymes; flavonoids; tensioning agents such as synthetic polymers, plant proteins, polysaccharides of plant origin optionally in the form of microgels, starches, wax dispersions, mixed silicates and colloidal particles of mineral fillers; ceramides; calmatives; mattifying agents; agents for preventing hair loss and/or for promoting regrowth of the hair; antiwrinkle active agents; skin whitening agents; emollient agents (e.g., diisopropyl sebacate); essential oils; and mixtures thereof; and any active agent that is suitable for the final aim of the composition.

Preparation

The compositions of the present invention can be prepared according to conventional methods, for example, according to a process in which the oily phase is emulsified in the aqueous phase with appropriate stirring, i.e. at an appropriate degree of shear. In particular, the compositions of the present invention can be prepared according to a process in which the oily phase is introduced into the aqueous phase with appropriate shear.

Intended Application

The compositions of the present invention are intended for topical application as sunscreen cosmetics and can constitute a composition intended for absorbing ultraviolet light, and/or for protecting a keratin substance especially of human from ultraviolet radiation. As examples of the keratin substance, mention may be made of the skin including lips and nails, and hair including eyelashes. It is well known in the art that protection of the keratin substance from ultraviolet radiation results in anti-ageing, anti-wrinkle, and moisturizing. Accordingly, the composition of the present invention can further constitute a composition intended for anti-aging, anti-wrinkle and/or moisturizing. Also, the compositions of the present invention can constitute a composition intended, for example, for treating, cleansing and making up a keratin substance, especially human skin, lips, hair, eyelashes and nails.

Thus, the present invention can also relates to a method of protecting a keratin substance from ultraviolet radiation comprising applying to the keratin substance the composition according to the present invention, as well as a method of absorbing ultraviolet light comprising applying the composition according to the present invention and subjecting the keratin substance to ultraviolet light. These methods can be defined as non-therapeutic methods.

EXAMPLES

The present invention will be described in more detail by way of examples, which however should not be construed as limiting the scope of the present invention.

Examples 1 to 5 and Comparative Examples 1 to 2

The preparation method and the evaluation methods of compositions in Examples 1 to 5 and Comparative Examples 1 to 2 are described below. Further the formulations of the compositions are shown in Table 1. The results of the evaluation methods are shown in Table 2.

Preparation Method

In each of Examples 1 to 5 and Comparative Examples 1 to 2, components of PHASE A in Table 1 were mixed under heating at 75-80° C. to give an aqueous phase. Separately, components of PHASE B in Table 1 were mixed under heating at 75-80° C. to give an oily phase. The resulting aqueous phase (PHASE A) and oily phase (PHASE B) were homogenized at 7,000 rpm for 5 minutes and then cooled to the room temperature (about 25° C.). Then, components of PHASE C and PHASE D in Table 1 were individually added thereto and mixed to yield the composition in the form of an O/W emulsion.

TABLE 1

| PHASE | COMPONENTS | Example 1 % | Example 2 % | Example 3 % | Example 4 % | Example 5 % | Comparative Example 1 % | Comparative Example 2 % |
|---|---|---|---|---|---|---|---|---|
| A | WATER | q.s. 100 | q.s. 100 | q.s. 100 | q.s. 100 | q.s. 100 | q.s. 100 | q.s. 100 |
|  | PROPYLENE GLYCOL | 2 | 2 | 2 | 2 | 2 | 2 | 2 |
|  | PHENOXYETHANOL | 0.4 | 0.4 | 0.4 | 0.4 | 0.4 | 0.4 | 0.4 |
|  | DISODIUM EDTA | 0.1 | 0.1 | 0.1 | 0.1 | 0.1 | 0.1 | 0.1 |
|  | INULIN LAURYL CARBAMATE (INUTEC SL1 by Creachem) | 0.25 | 0.25 | 0.25 | 0.25 | 0.25 | 0.25 | 0.25 |
| B | DIISOPROPYL SEBACATE | 5 | 5 | 5 | 5 | 5 | 5 | 5 |
|  | ETHYLHEXYL METHOXYCINNAMATE | 6.5 | 6.5 | 6.5 | 6.5 | 6.5 | 6.5 | 6.5 |
|  | DROMETRIZOLE TRISILOXANE | 3 | 3 | 3 | 3 | 3 | 3 | 3 |
|  | BIS-ETHYLHEXYLOXY PHENOL METHOXYPHENYL TRIAZINE | 3 | 3 | 3 | 3 | 3 | 3 | 3 |
|  | GLYCERYL STEARATE (and) PEG-100 STEARATE (SIMULSOL 165 by SEPPIC) |  |  |  |  |  |  | 1 |
|  | TITANIUM DIOXIDE (and) ALUMINUM HYDROXIDE (and) STEARIC ACID (MICRO TITANIUM DIOXIDE MT-100 T V by Tyca) | 2.5 | 2.5 | 2.5 | 2.5 | 2.5 | 2.5 | 2.5 |
| C | XANTHAN GUM | 0.1 | 0.1 | 0.1 | 0.1 | 0.1 | 0.1 | 0.1 |
|  | AMMONIUM POLYACRYLOYLDIMETHYL TAURATE | 0.4 | 0.4 | 0.4 | 0.4 | 0.4 | 0.4 | 0.4 |
|  | ALCOHOL DENAT. | 5 | 5 | 5 | 5 | 5 | 5 | 5 |
| D | PEG-12 DIMETHICONE (XIAMETER OFX-0193 FLUID by Dow Corning) | 0.5 | 1 | 0.5 | 0.5 | 0.5 |  |  |
|  | PEG-11 METHYL ETHER DIMETHICONE (KF 351 A by Shin Etsu) |  |  | 0.5 |  |  |  |  |
|  | PEG-10 DIMETHICONE (KF-6017 by Shin Etsu) |  |  |  | 0.5 |  |  |  |
|  | PEG-9 POLYDIMETHYL SILOXYETHYL DIMETHICONE (KF 6028 by Shin Etsu) |  |  |  |  | 0.5 |  |  |

Evaluation Methods

1. In Vitro Film Homogeneity Measurement

Each composition was applied on polypropylene sheet (0.2 mm PX-P from Sekisui Kagaku Co. Ltd) by an applicator called "Elecometer 4340" with the weight of 1 kg. Then the resulting sheet was exposed by UV lamp (UV black ray B-100AP; wave length 365 nm). The sheet to which the composition having good film homogeneity had been applied was observed as homogeneous dark intensive black. On the other hand, the sheet to which the composition having poor film homogeneity had been applied was observed as nonhomogeneous blue translucent film. The UV exposed sheet was taken pictures and scored from 1 to 5. (1 is low film homogeneity, 5 is high film homogeneity). Results of the evaluations were shown in Table 2.

2. In Vitro Protocol for Evaluating the Screening Efficacy

The sun protection factor (SPF) is determined according to the "in vitro" method described by B. L. Diffey in J. Soc. Cosmet. Chem. 40, 127-133, (1989). The measurements were made using a UV-2000 spectrophotometer from the company Labsphere. Each composition was applied to polypropylene sheet (0.2 mm PX-P from Sekisui Kagaku Co. Ltd) by an applicator called "Elecometer 4340" with the weight of 1 kg. SPF in vitro value was measured in 3 times to estimate an average value (SPF average). Results of the measurements were shown in Table 2.

3. Protocol for Evaluating the Watery Fresh Sensory During Application to the Skin The watery fresh sensory during application of each composition to the skin was evaluated by applying the composition to a forearm at a rate of 2 mg/cm$^2$ and then assessing the friction force felt between the fingers and the surface of the forearm by sensory experts. Wateriness and less stickiness were judged Yes or No. Results of the evaluations were shown in Table 2.

TABLE 2

|  |  | Example 1 | Example 2 | Example 3 | Example 4 | Example 5 | Comparative Example 1 | Comparative Example 2 |
|---|---|---|---|---|---|---|---|---|
| FILM HOMOGENEITY (SCORE) | | 4 | 4 | 4.5 | 4.5 | 4.5 | 2 | 4 |
| SPF in vitro | 1 | 39 | 35 | 45 | 65 | 64 | 7 | 58 |
|  | 2 | 30 | 32 | 34 | 57 | 55 | 10 | 61 |
|  | 3 | 29 | 29 | 34 | 55 | 54 | 10 | 62 |
|  | SPF average | 32.7 | 32.0 | 37.7 | 59.0 | 57.7 | 9 | 60.3 |
| SENSORY EVALUATION | watery | YES | YES | YES | YES | YES | YES | NO |
|  | less stickness | YES | YES | YES | YES | YES | YES | NO |

The composition of Comparative Example 1 had poor film homogeneity (i.e., inhomogeneous spreading) and good watery fresh sensory (i.e., watery skin sensation). Further, poor film homogeneity resulted in significant decrease in the efficacy (i.e., SPF value).

The compositions of Examples 1 to 5 contained polyether modified silicone as a specific surfactant and had good film homogeneity and good watery fresh sensory. That is, the addition of the specific surfactant resulted in the enhanced film homogeneity.

On the other hand, the composition of Comparative Example 2 additionally contained other surfactant than specific ones used in Examples 1 to 5, and had good film homogeneity and poor watery fresh sensory. That is, the addition of other surfactant than the specific ones resulted in undesired decrease in watery fresh sensory.

The compositions of Examples 3 to 5 contained two or more types of polyether modified silicones as specific surfactants in an amount of 1% in total and resulted in significant increase in the efficacy (i.e., SPF value). That is, combination of two or more types of polyether modified silicones has a synergistic effect.

Therefore only the compositions of all Examples provided had good film homogeneity and good watery fresh sensory.

Example 6

Components of PHASE A and PHASE B in Table 3 were mixed under heating at 70° C., and components of PHASE C in Table 3 were added and mixed, and then components of PHASE D were added and mixed under heating at 30° C. The mixture was neutralized by adding components of PHASE E to yield the composition in the form of an O/W emulsion.

TABLE 3

| PHASE | COMPONENTS | % |
|---|---|---|
| A | WATER | q.s. 100 |
|  | GLYCERIN | 4 |
|  | PROPYLENE GLYCOL | 3.6 |
|  | POTASSIUM CETYL PHOSPHATE | 1 |
|  | DISODIUM EDTA | 0.1 |
|  | INULIN LAURYL CARBAMATE (INUTEC SL1 by Creachem) | 0.1 |
|  | TEREPHTHALYLIDENE DICAMPHOR SULFONIC ACID | 4 |
|  | DISODIUM STEAROYL GLUTAMATE | 0.2 |
|  | SODIUM METHYL STEAROYL TAURATE | 0.2 |
| B | STEARIC ACID | 2 |
|  | GLYCERYL STEARATE (and) PEG-100 STEARATE (SIMULSOL 165 by SEPPIC) | 1 |
|  | CETYL ALCOHOL | 0.7 |
|  | BIS-ETHYLHEXYLOXYPHENOL METHOXYPHENYL TRIAZINE | 1 |
|  | ETHYLHEXYL METHOXYCINNAMATE | 7 |

TABLE 3-continued

| PHASE | COMPONENTS | % |
|---|---|---|
|  | DROMETRIZOLE TRISILOXANE | 4 |
|  | TITANIUM DIOXIDE (and) ALUMINUM HYDROXIDE (and) STEARIC ACID (MICRO TITANIUM DIOXIDE MT-100 T V by Tyca) | 2 |
| C | DIMETHICONE | 4 |
|  | CARBOMER | 0.2 |
|  | AMMONIUM ACRYLOYLDIMETHYLTAURATE/ VP COPOLYMER (ARISTOFLEX AVC by Clariant) | 0.4 |
| D | PEG-12 DIMETHICONE (XIAMETER OFX-0193 FLUID by Dow Corning) | 0.5 |
| E | TRIETHANOLAMINE | 2 |

The invention claimed is:

1. A composition in the form of an oil-in-water emulsion comprising:
   a) at least one inulin hydrophobically modified with alkyl carbamate groups,
   b) at least one silicone having a monovalent group selected from polyoxyalkylene groups, and
   c) at least one UV filter.

2. The composition according to claim 1, in which the inulin hydrophobically modified with alkyl carbamate groups is present in a content ranging from about 0.01 to about 10% by weight relative to the total weight of the composition.

3. The composition according to claim 1, in which the inulin hydrophobically modified with alkyl carbamate groups is based on chicory inulin.

4. The composition according to claim 1, in which the inulin hydrophobically modified with alkyl carbamate groups is present in a content ranging from about 0.1 to about 5% by weight relative to the total weight of the composition.

5. The composition according to claim 1, in which a hydrophobic group in the inulin hydrophobically modified with alkyl carbamate groups is selected from $C_4$-$C_{32}$ alkyl carbamate groups.

6. The composition according to claim 1, in which the inulin hydrophobically modified with alkyl carbamate groups is based on inulin lauryl carbamate.

7. The composition according to claim 1, in which the silicone having a monovalent group selected from polyoxyalkylene groups is present in a content ranging from about 0.01 to about 10% by weight relative to the total weight of the composition.

8. The composition according to claim 1, in which the silicone having a monovalent group selected from polyoxyalkylene groups is selected from polyoxyethylene modified dimethicones.

9. The composition according to claim 1, in which the silicone having a monovalent group selected from polyoxyalkylene groups is present in a content ranging from about 0.05 to about 5% by weight relative to the total weight of the composition.

10. The composition according to claim 1, in which the silicone having a monovalent group selected from polyoxyalkylene groups is a silicone having a monovalent group selected from polyoxy $C_2$-$C_8$ alkylene groups.

11. The composition according to claim 1, in which the UV filter is present in a content ranging from about 0.01 to about 30% by weight relative to the total weight of the composition.

12. The composition according to claim 1, in which the UV filter is an organic UV filter, or is a combination of an organic UV filter and an inorganic UV filter.

13. The composition according to claim 1, in which the UV filter is selected from the group consisting of drometrizole trisiloxane, ethylhexyl methoxycinnamate, bis-ethylhexyloxyphenol methoxyphenyl triazine, $TiO_2$ and mixtures thereof.

14. The composition according to claim 1, in which the UV filter is present in a content ranging from about 0.1 to about 25% by weight relative to the total weight of the composition.

15. The composition according to claim 1, in which the composition comprises water in a content ranging from 50 to 95% by weight relative to the total weight of the composition.

16. The composition according to claim 1, in which the composition comprises water in a content ranging from 60 to 90% by weight relative to the total weight of the composition.

17. The composition according to claim 1, in which the inulin hydrophobically modified with alkyl carbamate groups is present in a content ranging from about 0.15 to about 3% by weight, the silicone having a monovalent group selected from polyoxyalkylene groups is present in a content ranging from about 0.1 to about 2% by weight, and the UV filter is present in a content ranging from about 0.1 to about 25% by weight, all weight percentages being relative to the total weight of the composition.

18. A method of protecting a keratin substance from ultraviolet radiation comprising applying to the keratin substance the composition according to claim 1.

19. A method of absorbing ultraviolet light comprising applying the composition according to claim 1 to a keratin substance and subjecting the keratin substance to ultraviolet light.

* * * * *